United States Patent [19]

Stone et al.

[11] Patent Number: 5,401,256

[45] Date of Patent: Mar. 28, 1995

[54] FLEXIBLE CLAMP FOR USE IN IV TUBING SET

[75] Inventors: Stanford C. Stone, Woodbury, Minn.; John A. Howard, Jr., Houlton, Wis.

[73] Assignee: Minnesota Mining and Manufacturing Company, St. Paul, Minn.

[21] Appl. No.: 182,394

[22] Filed: Jan. 14, 1994

[51] Int. Cl.⁶ .......................... A61M 5/00; F16K 7/04
[52] U.S. Cl. ................................ 604/250; 604/246; 251/7; 251/10
[58] Field of Search ...................... 251/7–10; 604/246, 250, 30, 34; 128/DIG. 12

[56] References Cited

U.S. PATENT DOCUMENTS

| | | |
|---|---|---|
| 820,216 | 5/1906 | Leffingwell . |
| 1,243,054 | 10/1917 | Eager ........................ 604/250 X |
| 1,968,454 | 7/1934 | Hyatt ........................ 251/5 |
| 2,715,905 | 8/1955 | Ogle . |
| 2,722,932 | 11/1955 | Hickey . |
| 2,806,482 | 9/1957 | Norris et al. ........................ 137/376 |
| 2,832,560 | 4/1958 | Grigsby ........................ 251/9 |
| 2,889,848 | 6/1959 | Redner ........................ 137/315 |
| 3,216,418 | 11/1965 | Scislowicz . |
| 3,316,935 | 5/1967 | Kaiser et al. ........................ 137/595 |
| 3,390,860 | 7/1968 | Kavanau ........................ 251/9 |
| 3,539,081 | 11/1970 | Norton et al. ........................ 222/185 |
| 3,698,681 | 10/1972 | Lacey ........................ 251/10 |
| 3,822,052 | 7/1974 | Lange ........................ 251/10 |

(List continued on next page.)

FOREIGN PATENT DOCUMENTS

| | | | |
|---|---|---|---|
| 0186509 | 7/1986 | European Pat. Off. | ....... A61M 5/14 |
| 0205234 | 12/1986 | European Pat. Off. | ....... A61M 5/14 |
| 0238227 | 9/1987 | European Pat. Off. | ....... A61M 5/14 |
| 0319279 | 6/1989 | European Pat. Off. | ....... A61M 5/14 |
| 0415021 | 3/1991 | European Pat. Off. | ....... F16K 7/06 |
| 0510881 | 10/1992 | European Pat. Off. | .... A61M 39/00 |
| 1213861 | 4/1960 | France . | |
| 2590645 | 5/1987 | France | .......... F16K 21/00 |
| 2743239 | 4/1979 | Germany | ........ F16L 55/14 |
| 2953646 | 6/1981 | Germany | .......... A61B 19/00 |
| 203922 | 4/1939 | Switzerland . | |
| 1225812 | 3/1971 | United Kingdom | ......... D06F 55/02 |

OTHER PUBLICATIONS

Brochure entitled "Gemini Administration Sets" by IMED Corporation, 1987.
Flyer entitled "AVI 480 Infusion Pump With Free--Flow Prevention" by 3M Health Care, No. 70-2008046-32-0 (May, 1990).

Primary Examiner—John D. Yasko
Assistant Examiner—Adam J. Cermak
Attorney, Agent, or Firm—Gary L. Griswold; Walter N. Kirn; Stephen W. Bauer

[57] ABSTRACT

A flexible clamp for IV tubing, and in particular for use in a free flow prevention system. The flexible clamp has a pair of generally elongate clamping arms defining a slot for receiving the IV tubing. The flexible clamp has a resilient bias tending to bring the clamping arms to a closed position wherein the IV tubing is squeezed between the clamping arms to close the lumen of the IV tubing to prevent fluid flow, and the clamping arms are movable against the resilient bias of the flexible clamp to an open position wherein the clamping arms are spread from one another relative to the closed position such that the lumen of the IV tubing is allowed to open so that flow through the lumen of the IV tubing is permitted. Complementary interlocking structures on the free ends of the clamping arms are brought into interlocking relationship when the clamping arms are brought to their closed position, thereby tending to prevent skewing of the free ends of the clamping arms out of the plane of motion of the clamping arms.

31 Claims, 5 Drawing Sheets

U.S. PATENT DOCUMENTS

| | | | |
|---|---|---|---|
| 3,942,228 | 3/1976 | Buckman et al. | 24/255 |
| 4,091,815 | 5/1978 | Larsen . | |
| 4,097,020 | 6/1978 | Sussman | 251/10 |
| 4,193,174 | 3/1980 | Stephens | 24/249 |
| 4,247,076 | 1/1981 | Larkin | 251/7 |
| 4,248,401 | 2/1981 | Mittleman | 251/7 |
| 4,369,951 | 1/1983 | Marsoner et al. | 251/7 |
| 4,434,963 | 3/1984 | Russell | 251/7 |
| 4,460,358 | 7/1984 | Somerville et al. | 604/250 |
| 4,487,205 | 12/1984 | Di Giovanni et al. | 251/10 X |
| 4,519,792 | 5/1985 | Dawe | 604/152 |
| 4,560,378 | 12/1985 | Weiland | 604/83 |
| 4,585,441 | 4/1986 | Archibald | 604/245 |
| 4,585,442 | 4/1986 | Mannes | 604/250 |
| 4,586,691 | 5/1986 | Kozlow | 251/7 |
| 4,589,626 | 5/1986 | Kurtz et al. | 251/10 |
| 4,645,175 | 12/1987 | Kamen | 251/9 |
| 4,673,161 | 6/1987 | Flynn et al. | 251/10 |
| 4,689,043 | 8/1987 | Bisha | 604/250 |
| 4,802,650 | 2/1989 | Stricker | 251/117 |
| 4,818,190 | 4/1989 | Pelmulder et al. | 417/360 |
| 4,944,485 | 7/1990 | Daoud et al. | 251/9 |
| 5,017,192 | 5/1991 | Dodge et al. | 604/250 |
| 5,035,399 | 7/1991 | Rantanen-Lee | 251/10 |
| 5,201,711 | 4/1993 | Pasqualucci et al. | 604/153 |
| 5,290,239 | 3/1994 | Classey et al. | 604/131 |
| 5,300,044 | 4/1994 | Classey et al. | 604/250 |

FLEXIBLE CLAMP FOR USE IN IV TUBING SET

The invention relates generally to IV tubing sets for the controlled delivery of fluids to a patient, and more particularly to a free flow prevention system and flexible clamp for preventing free flow of fluid through the IV tubing when the tubing is disconnected from an infusion pump.

BACKGROUND OF THE INVENTION

Infusion pumps are typically used to regulate the delivery of fluids, which may include potentially hazardous drugs, to a patient with a high degree of accuracy. Until a few years ago, in order to prevent "free flow" or "fluid runaway" a roller clamp was moved to a closed position to stop flow through IV tubing without the tubing is removed from an infusion pump. "Free flow" or "fluid runaway" is an undesirable situation where fluid is free to flow rapidly through the IV tubing without regulation by the infusion pump. Such roller clamps are effective in preventing free flow only when they are manually moved to their closed positions, and free flow or fluid runaway may occur if the roller clamp is left in its open position. As a result, automatic free flow prevention systems have recently been provided in which fluid runaway is prevented regardless of whether the pump operator remembers to close a roller or slide clamp.

One preferred free flow prevention system is described in co-assigned U.S. Pat. No. 5,017,192. This system employs a flexible clamp having clamping arms defining a variable width slot. The clamping arms are biased to a closed position in which the lumen of the IV tubing is closed to fluid flow. During operation of the infusion pump, a clamp-opening wedge in the infusion pump spreads the clamping arms to the open position to allow the lumen of the IV tubing to open to fluid flow. This free flow prevention system has been a successful and easy to use method of preventing free flow.

Another approach is described in co-assigned U.S. Pat. No. 4,585,441 wherein an interlock is provided to prevent removal of the IV set unless fluid flow through the tubing is stopped. The pump operator must manually close a clamp to stop fluid flow through the tubing before the infusion pump will permit removal of the IV set.

Co-assigned U.S. patent application Ser. No. 08/070,497, filed Jun. 1, 1993, which is a continuation of Ser. No. 07/690,819, filed Apr. 23, 1991, on Free Flow Prevention System for Infusion Pump, describes a flexible spring clip that is particularly adapted for use with a pumping cassette of the type described in co-assigned U.S. Pat. Nos. 4,236,880; 4,277,226; 4,322,201; 4,382,753; 4,391,600; and 4,410,322.

Other approaches include employing slide clamps to prevent or reduce the risk of removing the IV set without closing a clamp. U.S. Pat. Nos. 4,586,691; 4,689,043 and 4,818,190 describe employing slide clamps to prevent fluid runaway during removal of IV sets from infusion pumps.

U.S. Pat. No. 4,944,485 describes a clamp having a pair of clamping members pivotally hinged together and biased to clamp a segment of IV tubing. That clamp also includes a latch for latching the clamp in an open position.

SUMMARY OF THE INVENTION

The invention provides a free flow prevention system and novel flexible clamp adapted for preventing free flow of fluid through IV tubing when the tubing is disconnected from an infusion pump. The system and novel flexible clamp are designed to be easy to use, and to automatically close the IV tubing to fluid flow when the tubing is disconnected from the infusion pump.

Generally, the flexible clamp of the invention has a pair of generally elongate clamping arms defining a slot for receiving the IV tubing. The flexible clamp has a resilient bias tending to bring the clamping arms to a closed position wherein the IV tubing is squeezed between the clamping arms to close the lumen of the IV tubing to prevent fluid flow. The clamping arms are movable against the resilient bias of the flexible clamp to an open position wherein the clamping arms are spread from one another relative to the closed position such that the lumen of the IV tubing is allowed to open so that flow through the lumen of the IV tubing is permitted. The free ends of the clamping arms are movable relative to one another as the clamping arms are moved between their closed and open positions. Cooperable alignment means is provided on each clamping arm generally adjacent the free end of the clamping arm and cooperable with the cooperable alignment means of the other clamping arm for aligning the free ends of each clamping arm relative to one another when the clamping arms are in their closed position. The alignment means tend to prevent skewing of the clamping arms when the clamping arms are in their closed position.

Preferably, the clamping arms define a plane of motion along which the clamping arms move between their closed and open positions, and the cooperable alignment means comprises complementary interlocking structures on the free ends of the clamping arms that are brought into interlocking relationship when the clamping arms are brought to their closed position. Most preferably, the complementary interlocking structures comprise complementary projecting and recessed portions on each clamping arm. For example, the projecting and recessed portions of one clamping arm define an opposite or negative structure compared to the projecting and recessed portions of the other clamping arm.

Most preferably, the projecting portions of either clamping arm are closely received in the recessed portions of the other clamping arm when the clamping arms are in their closed position.

Also, preferably, the interlocking structures of the clamping arms are brought into pressing interengagement with one another when the clamping arms are in their closed position.

In another aspect of the invention, a tubing set is provided incorporating the flexible clamp of the invention. The IV tubing has an outside diameter, and the slot defined by the clamping arms is a variable width slot along which the IV tubing may be moved between first and second positions. In the first position, the width of the slot is relatively wide to permit the clamp to be positioned longitudinally along the IV tubing but is no wider than the outside diameter of the IV tubing so that the flexible clamp tends to hold its longitudinal position along the IV tubing. In the second position, the width of the slot is normally less than the width of the slot in the first position and the clamping arms when in their closed position close the lumen of the IV tubing to fluid flow.

Most preferably, the width of the wide portion of the slot is slightly smaller than the outside diameter of the IV tubing to hold the flexible clamp in position along the IV tubing without closing the lumen of the IV tubing to fluid flow.

In yet another aspect of the invention, the flexible clamp is incorporated into a free flow prevention system comprising an infusion pump and an IV tubing set.

Other features will be in part apparent and in part pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION

Figure 1:
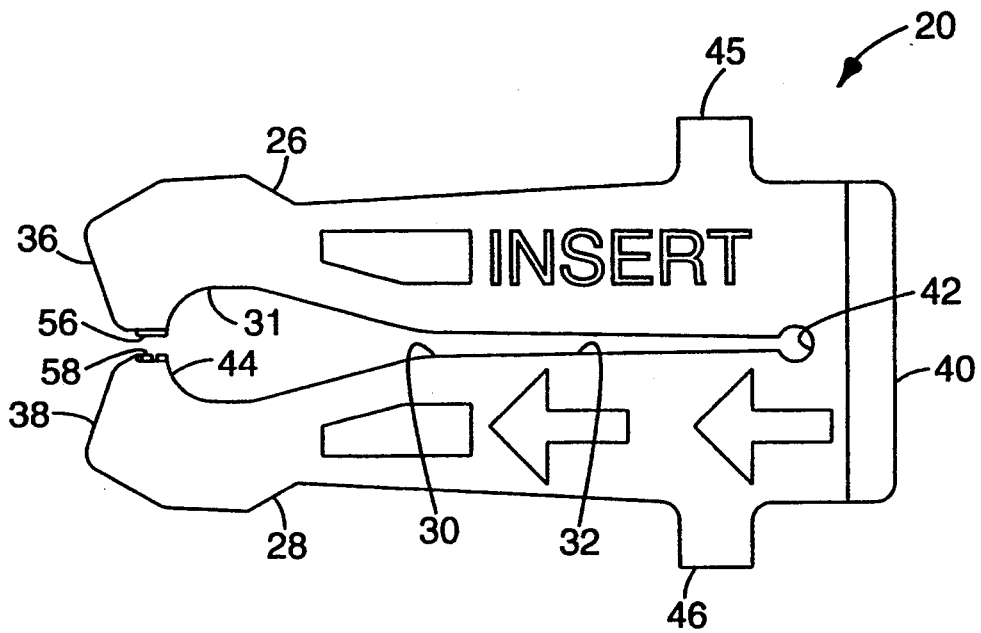
FIG. 1 is an enlarged top plan view of a novel flexible clamp of the invention.
Figure 8:
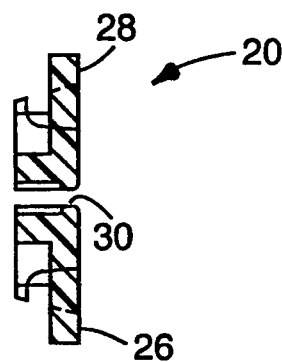
FIG. 8 is a cross-sectional view substantially along line 8—8 of FIG. 2.
Figure 3:
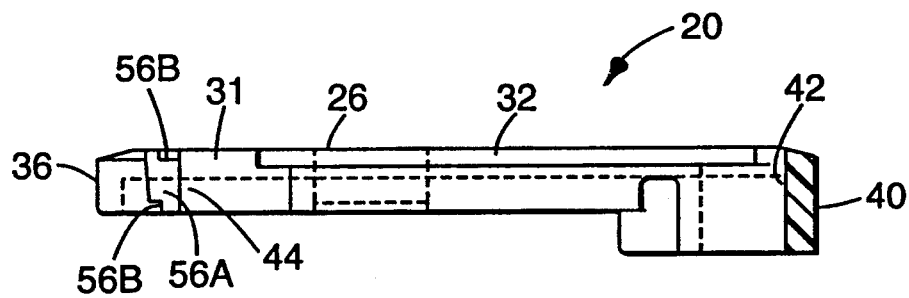
FIG. 3 is a longitudinal cross-sectional view substantially along line 3—3 of FIG. 2.
Figure 2:
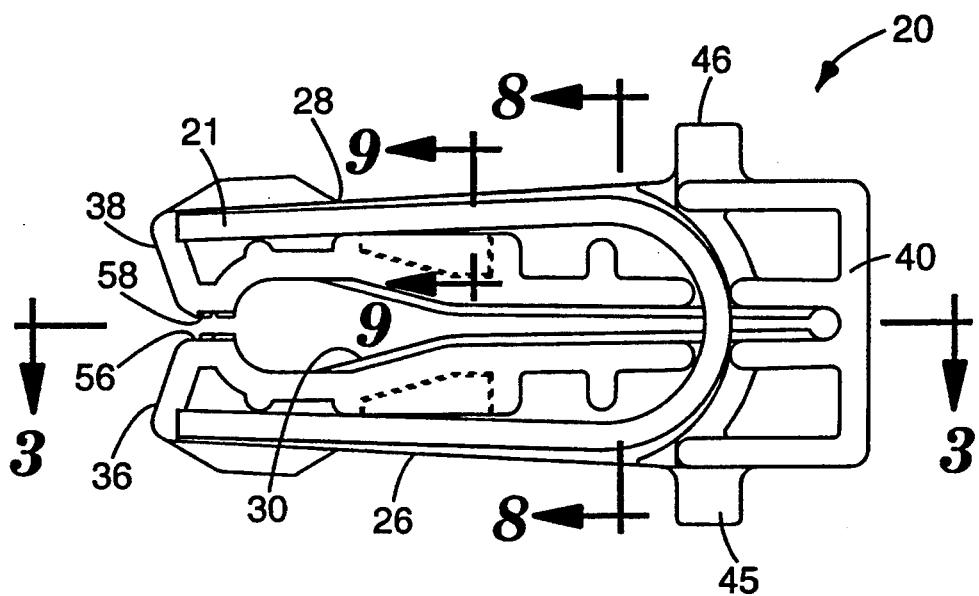
FIG. 2 is an enlarged bottom plan view of the flexible clamp of FIG. 1.

Now referring to the drawing, in particular FIGS. 1 and 2, a novel flexible clamp of the invention is designated in its entirety by the reference numeral 20. The flexible clamp 20 is an improvement upon the successful flexible clamp shown in co-assigned U.S. Pat. No. 5,017,192, which is hereby incorporated herein by reference. The flexible clamp 20 is particularly adapted for use in the free flow prevention system described in U.S. Pat. No. 5,017,192 in order to prevent undesired free flow of fluid through IV tubing 22 when the IV tubing 22 is disconnected from an infusion pump 24 regulating fluid flow to a patient.

The IV tubing set 22 and infusion pump 24 also preferably are of the general type described in U.S. Pat. Nos. 4,236,880; 4,277,226; 4,322,201; 4,382,753; 4,391,600; 4,410,322; 5,017,192; 5,103,214; 5,203,943 and 5,242,407; and co-pending U.S. patent application Ser. Nos. 07/797,691, filed Nov. 25, 1991; 07/976,404, filed Nov. 13, 1992; 08/076,813, filed Jun. 14, 1993; and D-07/917,611, filed Jul. 23, 1992 (all of which are incorporated herein by reference). Such infusion pumps 24 are designed for use with IV tubing 22 that includes a pumping cassette (not shown) having flexible walls defining fluid pumping chambers which may be compressed to regulate fluid flow through the IV tubing. Infusion pumps of this type are sold by Minnesota Mining and Manufacturing Company of St. Paul, Minn.

The infusion pump 24 may alternatively be of the type commonly referred to as a "linear peristaltic pump", that is, pumps that selectively squeeze straight portions of the IV tubing to regulate or pump fluid through the IV tubing. In any event, the infusion pump 24 regulates fluid flow through the lumen of IV tubing 22 for administration to a patient.

As shown in FIGS. 1 and 2, like the clamp shown in U.S. Pat. No. 5,017,192, the flexible clamp 20 has a pair of clamping arms 26 and 28 defining a variable width slot 30. The IV tubing 22 may be moved along the variable width slot 30 between a first position (approximately at 31) and a second position (approximately at 32). In the first position 31, the width of the slot 30 is sufficient to permit the flexible clamp 20 to be positioned longitudinally along the IV tubing 22. At the second position 32, the width of the slot 30 is normally less than the width of the slot 30 at the first position 31.

Figure 13:
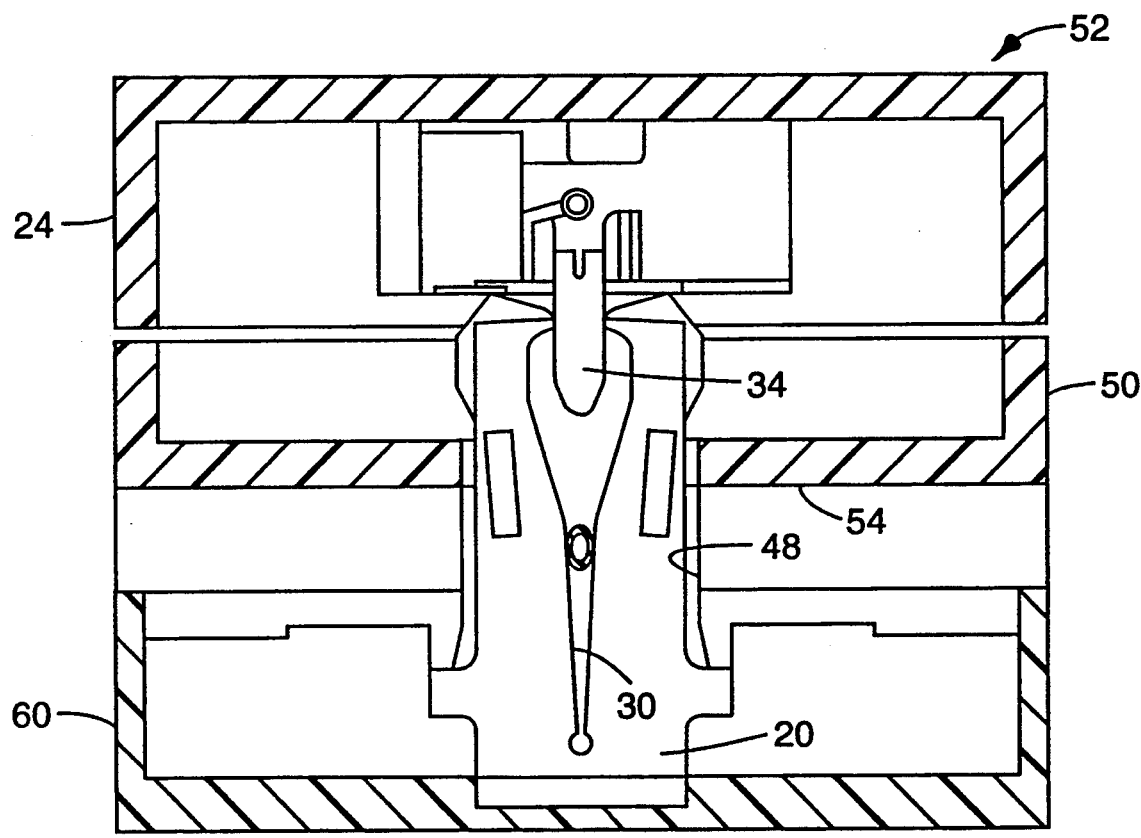
FIG. 13 is a cross-sectional view substantially along line 13—13 of FIG. 12, showing the novel flexible clamp of FIGS. 1-11.

The flexible clamp 20 has a resiliently bias tending to bring the clamping arms 26 and 28 to a closed position wherein the IV tubing 22 is squeezed when at the second position (line 11—11) to close the lumen of the IV tubing 22 to prevent fluid flow. For example, a resilient spring 21 of the type described in U.S. Pat No. 5,017,192 may provide such a resilient bias to the clamping arms 26 and 28. The clamping arms 26 and 28 are movable against the resilient bias of the flexible clamp 20 by a clamp-opening wedge 34 (FIG. 13) in the infusion pump 24 to an open position wherein the lumen of the IV tubing 22 is allowed to open so that flow through the lumen is permitted. The free ends 36 and 38 of the clamping arms 26 and 28 are movable relative to one another as the clamping arms 26 and 28 are moved between their closed and open positions.

The flexible clamp 20 preferably comprises a body (also 20) formed of thermoplastic or synthetic resin material, such as ABS plastic, and a resilient generally U-shaped spring member (not shown but described in U.S. Pat. No. 5,017,192) biasing the clamping arms 26 and 28 to their closed position. The body of the flexible clamp 20 includes a hinged bridging portion 40 defining an inner end 42 of the slot 30. The clamping arms 26 and 28 of the clamp 20 extend outwardly (leftwardly in FIGS. 1 and 2) from the bridging portion 40, and terminate in the free ends 36 and 38, which define the outer end 44 of the slot 30. The free ends 36 and 38 of the clamping arms 26 and 28 are tapered inwardly toward the slot 30 and bridging portion 40 to guide the clamp-opening wedge 34 into the outer end 44 of the slot 30 between the clamping arms 26 and 28.

The clamping arms 26 and 28 have inner surface portions between the inner end 42 of the slot 30 and their free ends 36 and 38, preferably generally adjacent their free ends 36 and 38, that define the first (wide) position 31. The inner end 42 of the slot 30 may be, for example, generally adjacent the second position 32, with a portion of the clamping arms 26 and 28 generally adjacent the bridging portion 40 defining an open area as the second (narrow) position 32. The slot 30 defines the longitudinal direction or axis of the clamp 20.

Abutment means, such as ledges 45 and 46 extending laterally outwardly from opposite sides of the clamp 20, may be provided on the clamp 20. The ledges 45 and 46 limit insertion of the clamp 20 into an elongate passageway 48 (FIG. 13) in the infusion pump 24 to a first predetermined distance, with the first and second positions 31 and 32 of the IV tubing 22 being spaced apart along the longitudinal axis of the clamp 20 a second predetermined distance substantially equal to the first predetermined distance. In other words, the ledges 45 and 46 are preferably spaced from the free ends 36 and 38 of the clamping legs 26 and 28 a distance substantially equal to the distance separating the first and second positions 31 and 32. A cassette-receiving block 50 of the pumping assembly 52 includes a wall 54 that substantially prevents movement of the IV tubing 22 into the passageway 48 as the clamp 20 is inserted into the passageway 48. The result is that the IV tubing 22 is moved from the first position 31 to the second position 32 by wall 54 when the clamp 20 is manually inserted in the passageway 48 to the first predetermined distance.

Unlike the clamp described in U.S. Pat. No. 5,017,192, novel cooperable alignment means 56 and 58 is provided on each clamping arm 26 and 28 generally adjacent the free ends 36 and 38 of the clamping arm 26 and 28. The alignment means 56 and 58 of each clamping arm 26 or 28 are cooperable with the cooperable alignment means 58 or 56 of the other clamping arm 28 or 26 in order to align the free ends 36 and 38 of each clamping arm 26 and 28 relative to one another when the clamping arms 26 and 28 are in their closed position. The cooperable alignment means 56 and 58 tend to prevent skewing of the clamping arms 26 and 28 when the clamping arms 26 and 28 are in their closed position.

The clamping arms 26 and 28 define a plane of motion along which the clamping arms 26 and 28 move between their closed and open positions. This plane of motion is along the plane of the drawing in FIGS. 1 and 2.

Preferably, as best illustrated in FIGS. 4–7, the cooperable alignment means 56 and 58 comprises complementary interlocking structures 56 and 58 generally adjacent the free ends 36 and 38 of the clamping arms 26 and 28. The complementary interlocking structures 56 and 58 are brought into interlocking relationship when the clamping arms 26 and 28 are brought to their closed position to thereby tend to prevent skewing of the free ends 36 and 38 of the clamping arms 26 and 28 out of the plane of motion of the clamping arms 26 and 28.

For example, the complementary interlocking structures 56 and 58 may comprise complementary projecting and recessed portions 56A, 56B, 58A and 58B on each clamping arms 26 and 28 such that the projecting and recessed portions 56A and 56B or 58A and 58B of one clamping arm 26 or 28 define an opposite or negative structure 56 or 58 compared to the projecting and recessed portions 58A and 58B or 56A and 56B of the other clamping arm 28 or 26. The arrangement is such that the projecting portions 56A or 58A of either clamping arm 26 or 28 are closely received in the recessed portions 58B or 56B of the other clamping arm 28 or 26 when the clamping arms 26 and 28 are in their closed position, thereby tending to prevent skewing of the free ends 36 and 38 of the clamping arms 26 and 28 out of the plane of motion of the clamping arms 26 and 28.

Figure 9:
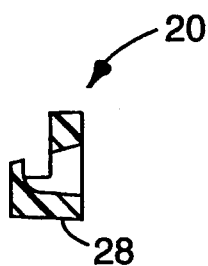
FIG. 9 is a cross-sectional view substantially along line 9—9 of FIG. 2.
Figure 11:
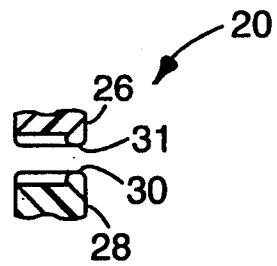
FIG. 11 is an enlarged cross-sectional view substantially along line 11—11 of FIG. 10 illustrating details of the variable width slot.
Figure 10:
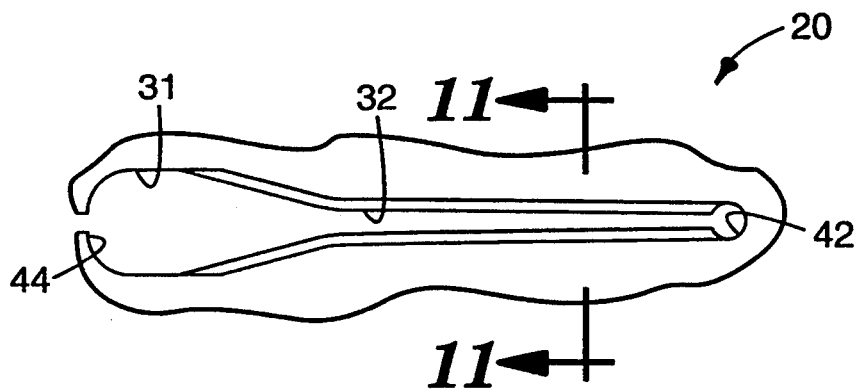
FIG. 10 is a view outlining a variable width slot of the flexible clamp of FIGS. 1-9.

Most preferably, the interlocking structures 56 and 58 of the clamping arms 26 and 28 are brought into pressing interengagement with one another when the clamping arms 26 and 28 are in their closed position. This may be accomplished by selecting a sufficiently strong resilient metal U-shaped spring member. FIG. 9 illustrates structural details of the clamp body (also 20) that relate to retaining the generally U-shaped spring member (not shown) in position on the flexible clamp 20.

Figure 6:
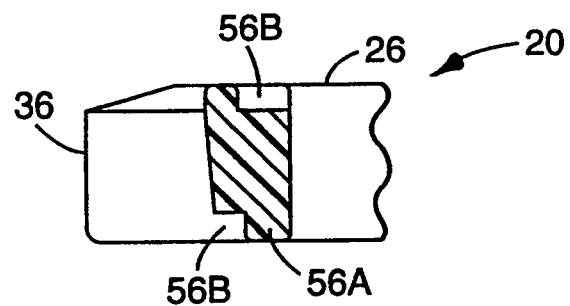
FIG. 6 is a view substantially along line 6—6 in FIG. 4, showing an interlocking structure adjacent the free end of one of the clamping arms of the flexible clamp of FIGS. 1-5.
Figure 5:
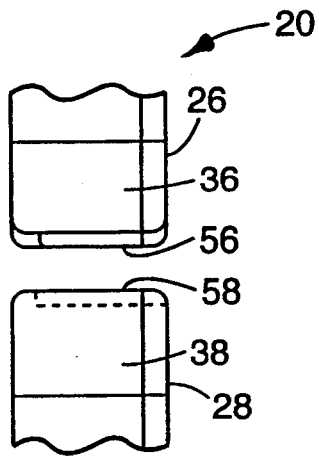
FIG. 5 is an end view of the free ends of the clamping arms of FIG. 4.
Figure 4:
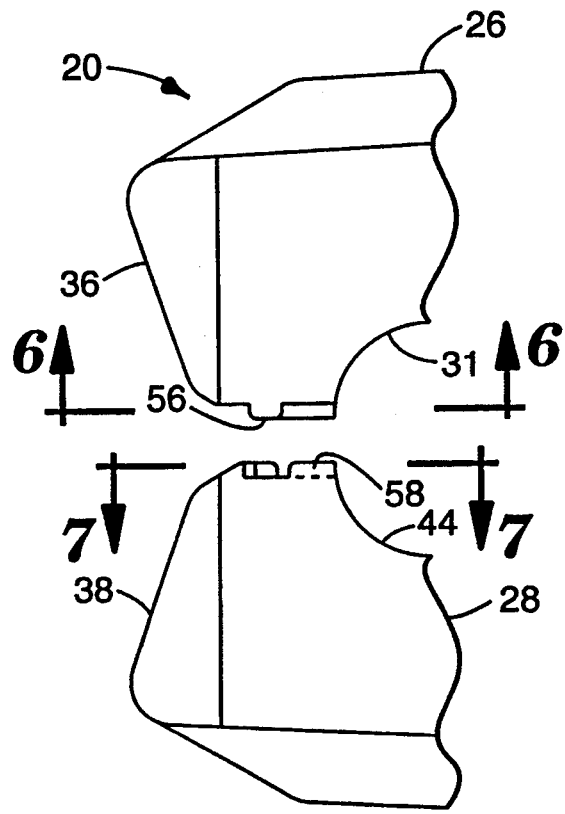
FIG. 4 is a further enlarged view of the free ends of the clamping arms of the flexible clamp of FIGS. 1-3.
Figure 7:
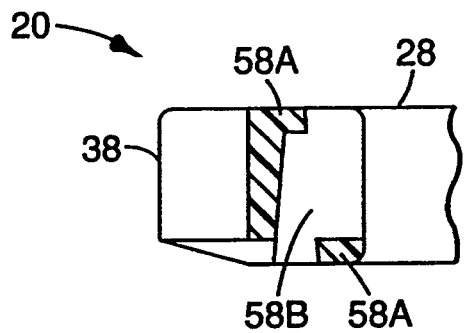
FIG. 7 is a view substantially along line 7—7 in FIG. 4, showing an interlocking structure adjacent the free end of the other clamping arm complementary to the interlocking structure of FIG. 6.

FIGS. 6 and 7 illustrate a preferred configuration and arrangement of projecting and recessed portions 56A, 56B, 58A and 58B. The illustrated projecting portions 56A and 58A preferably provide a substantially flat profile when viewed along the end of the flexible clamp 20 as in FIG. 5. This substantially flat profile extending substantially from side-to-side of the flexible clamp 20 helps to stabilize the clamping arms 26 and 28 to prevent skewing when the clamping arms 26 and 28 are held in their open position by engagement of the clamp-opening wedge 34 on the projecting portions 56A and 58A.

Also, unlike the flexible clamp described in U.S. Pat. No. 5,017,192, the wide portion 31 of the variable width slot 30 is sized the same as or slightly smaller than the outside diameter of the IV tubing 22 to frictionally engage the IV tubing 22 and hold the flexible clamp 20 linearly or longitudinally along the IV tubing 22 when the IV tubing 22 is in its first position 31 along the clamp 20. For example, the wide portion 31 of the slot 30 may have a width of approximately 0.125 inches (3.2 mm), and the IV tubing 22 may have an outside diameter of approximately 0.162 inches (4.1 mm). This arrangement helps to semi-permanently locate the flexible clamp 20 linearly or longitudinally along the IV tubing 22, as well as maintain a desired orientation radially with respect to the IV tubing 22. Maintaining the longitudinal and radial position of the flexible clamp 20 relative to the IV tubing 22 facilitates aligning the flexible clamp 20 relative to the clamp-receiving passageway 48 of the infusion pump 24 and inserting the flexible clamp 20 into the clamp-receiving passageway 48 when connecting the IV tubing set 22 to the infusion pump 24.

Also, preferably, the narrow portion such as at 32 of the slot 30 is molded at a slight angle such that the narrow portion of the slot 30 has a generally constant gap along its length when the flexible clamp 20 is in its closed position.

OPERATION

Other than as described above, operation of the flexible clamp 20 is similar to operation of the clamp described in U.S. Pat. No. 5,017,192. The flexible clamp 20 is used in association with an IV tubing set 22 having a lumen through which fluid may be pumped for administration to a patient.

The appropriate portion, e.g., a pumping cassette, of the IV tubing set 22 is positioned in the pumping assembly of the infusion pump 24 so that suitable pumping means can act on the pumping cassette to pump fluid through the IV tubing 22, and the flexible clamp 20 is inserted into the clamp-receiving passageway 48 in the infusion pump 24. Because the novel flexible clamp 20 tends to hold its longitudinal and radial position along the IV tubing 22 even when the IV tubing 22 is in its first position 31 along the slot 30, the flexible clamp 20 should be in position to be inserted into the clamp-receiving passageway 48 without adjustment by the operator. However, if the flexible clamp 20 is not correctly positioned, the flexible clamp 20 may be readily moved along the IV tubing 22 to adjust its position. The releasable holding means, such as a door 60, is then closed to hold the IV tubing set 22 and flexible clamp 20 during operation of the infusion pump 24.

Figure 12:
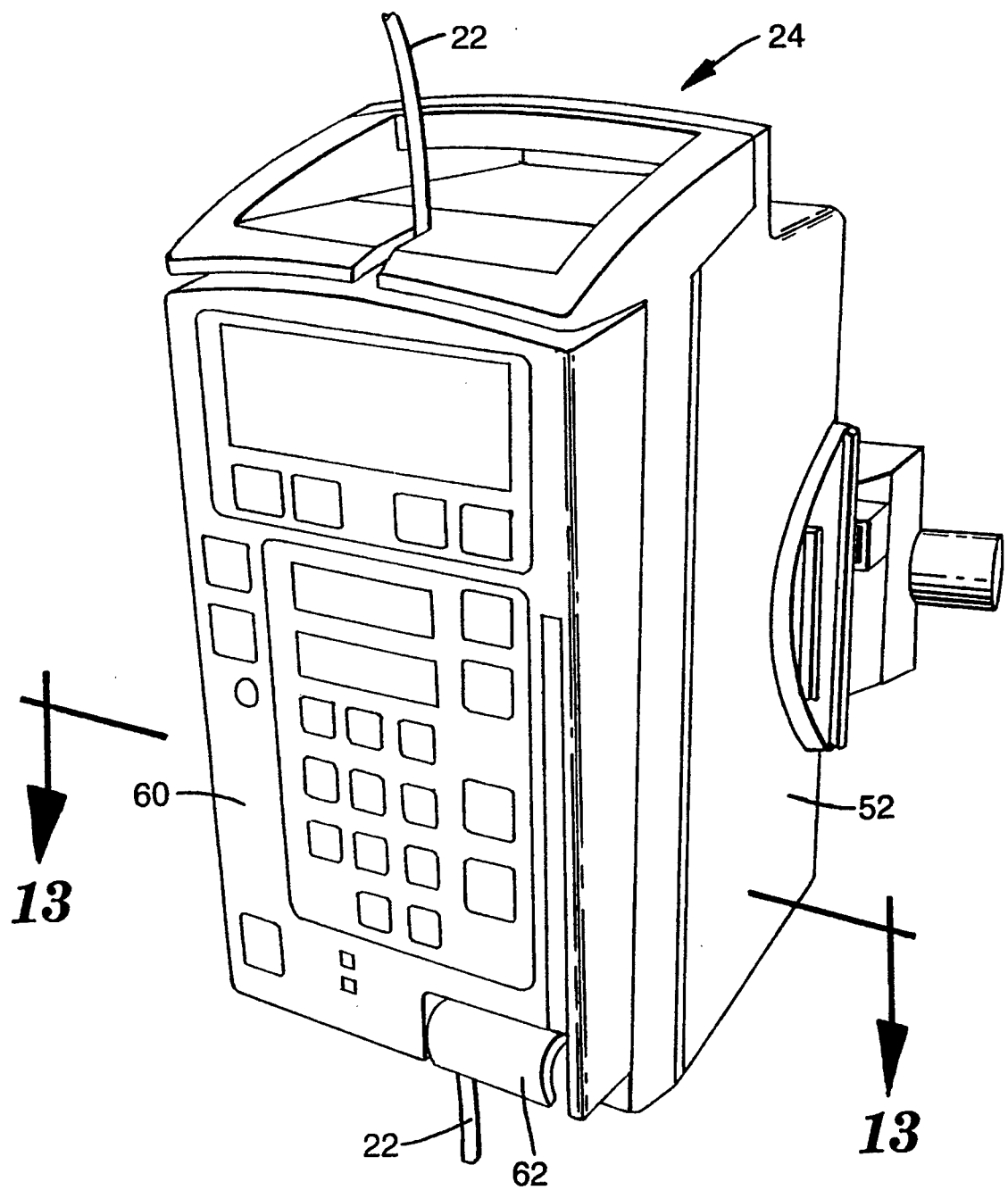
FIG. 12 is a perspective view of an infusion pump incorporating a free flow prevention system employing the flexible clamp of FIGS. 1-11.

When the door latch 62 is moved to its latched position (shown in FIG. 12), the releasable clamp-opening wedge 34 separates the clamping arms 26 and 28 of the flexible clamp 20 and moves the clamping arms 26 and 28 from their closed position to the open position to allow fluid flow through the IV tubing 22 during operation of the pumping assembly. When the door latch 62 is latched or unlatched, the clamp-opening wedge 34 moves relative to the flexible clamp 20 received in the clamp-receiving passageway 48 between an unloading position, wherein the clamp-opening wedge 34 does not hold the clamping arms 26 and 28 of the flexible clamp 20 in their open position, and an operating position, wherein the clamp-opening wedge 34 moves the clamping arms 26 and 28 of the flexible clamp 20 to their open position and holds the clamping arms 26 and 28 in the open position.

In order to remove the IV tubing set 22 from the pump 24, the door latch 62 is unlatched, thereby moving the clamp-opening wedge 34 relative to the clamp-receiving passageway 48 in the direction away from the flexible clamp 20 so that the clamp 20 returns to its closed position. The door 34 is then opened, and the IV tubing set 22, including the IV tubing 22 and flexible clamp 20, are removed from the infusion pump 20, with the lumen of the IV tubing 22 being closed due to the clamping action of the clamping arms 26 and 28 against the tubing 22 at the second position 32. As a result, free flow through the tubing 22 is prevented during and after disconnection of the IV tubing set regardless of whether a standard roller clamp (not shown) is closed.

As various changes could be made in the above constructions without departing from the scope of the invention as defined in the claims, it is intended that all matter contained in the above description or shown in the accompanying drawing be interpreted as illustrative and not in a limiting sense.

We claim:

1. In a flexible clamp for IV tubing having a lumen, the flexible clamp having a pair of generally elongate clamping arms defining a slot for receiving the IV tubing, the flexible clamp having a resilient bias tending to bring the clamping arms to a closed position wherein the IV tubing is squeezed between the clamping arms to close the lumen of the IV tubing to prevent fluid flow, the clamping arms being movable against the resilient bias of the flexible clamp to an open position wherein the clamping arms are spread from one another relative to the closed position such that the lumen of the IV tubing is allowed to open so that flow through the lumen of the IV tubing is permitted, the clamping arms having free ends movable relative to one another as the clamping arms are moved between their closed and open positions, the improvement comprising cooperable alignment means, on each clamping arm generally adjacent the free end of the clamping arm and cooperable with the cooperable alignment means of the other clamping arm, for aligning the free ends of each clamping arm relative to one another when the clamping arms are in their closed position, thereby tending to prevent skewing of the clamping arms when the clamping arms are in their closed position.

2. A flexible clamp according to claim 1 wherein the clamping arms define a plane of motion along which the clamping arms move between their closed and open positions, the cooperable alignment means comprises complementary interlocking structures on the free ends of the clamping arms that are brought into interlocking relationship when the clamping arms are brought to their closed position, thereby tending to prevent skewing of the free ends of the clamping arms out of the plane of motion of the clamping arms.

3. A flexible clamp according to claim 2 wherein the complementary interlocking structures comprise complementary projecting and recessed portions on each clamping arm such that the projecting and recessed portions of one clamping arm define an opposite or negative structure compared to the projecting and recessed portions of the other clamping arm.

4. A flexible clamp according to claim 2 wherein the complementary interlocking structures comprise complementary projecting and recessed portions on each clamping arm, the projecting portions of either clamping arm being closely received in the recessed portions of the other clamping arm when the clamping arms are in their closed position, thereby tending to prevent skewing of the free ends of the clamping arms out of the plane of motion of the clamping arms.

5. A flexible clamp according to claim 4 wherein the interlocking structures of the clamping arms are brought into pressing interengagement with one another when the clamping arms are in their closed position.

6. In a flexible clamp for preventing undesired free flow of fluid through IV tubing when the IV tubing is disconnected from an infusion pump regulating fluid flow to a patient, the clamp having a pair of clamping arms defining a variable width slot along which the IV tubing may be moved between a first position wherein the width of the slot is sufficient to permit the clamp to be positioned longitudinally along the IV tubing, and a second position wherein the width of the slot is normally less than the width of the slot at the first position, the flexible clamp having a resiliently bias tending to bring the clamping arms to a closed position wherein the IV tubing is squeezed when at the second position to close the lumen to prevent fluid flow, the clamping arms being movable against the resilient bias of the flexible clamp to an open position wherein the lumen of the IV tubing is allowed to open so that flow through the lumen is permitted, the clamping arms having free ends movable relative to one another as the clamping arms are moved between their closed and open positions, the improvement comprising cooperable alignment means, on each clamping arm generally adjacent the free end of the clamping arm and cooperable with the cooperable alignment means of the other clamping arm, for aligning the free ends of each clamping arm relative to one another when the clamping arms are in their closed position, thereby tending to prevent skewing of the clamping arms when the clamping arms are in their closed position.

7. A flexible clamp according to claim 6 wherein the clamping arms define a plane of motion along which the clamping arms move between their closed and open positions, the cooperable alignment means comprises complementary interlocking structures on the free ends of the clamping arms that are brought into interlocking relationship when the clamping arms are brought to their closed position, thereby tending to prevent skewing of the free ends of the clamping arms out of the plane of motion of the clamping arms.

8. A flexible clamp according to claim 7 wherein the complementary interlocking structures comprise complementary projecting and recessed portions on each clamping arms such that the projecting and recessed portions of one clamping arm define an opposite or negative structure compared to the projecting and recessed portions of the other clamping arm.

9. A flexible clamp according to claim 7 wherein the complementary interlocking structures comprise complementary projecting and recessed portions on each clamping arm, the projecting portions of either clamping arm being closely received in the recessed portions of the other clamping arm when the clamping arms are in their closed position, thereby tending to prevent skewing of the free ends of the clamping arms out of the plane of motion of the clamping arms.

10. A flexible clamp according to claim 9 wherein the interlocking structures of the clamping arms are brought into pressing interengagement with one another when the clamping arms are in their closed position.

11. In a flexible clamp for IV tubing having a lumen, the flexible clamp having a pair of generally elongate clamping arms defining a slot for receiving the IV tubing, the flexible clamp having a resilient bias tending to bring the clamping arms to a closed position wherein the IV tubing is squeezed between the clamping arms to close the lumen of the IV tubing to prevent fluid flow, the clamping arms being movable against the resilient bias of the flexible clamp to an open position wherein the clamping arms are spread from one another relative to the closed position such that the lumen of the IV tubing is allowed to open so that flow through the lumen of the IV tubing is permitted, the clamping arms having free ends movable relative to one another as the clamping arms are moved between their closed and open positions, the clamping arms defining a plane of motion along which the clamping arms move between their closed and open positions, the improvement comprising complementary interlocking structures on the free ends of the clamping arms that are brought into interlocking relationship when the clamping arms are brought to their closed position, thereby tending to prevent skewing of the free ends of the clamping arms out of the plane of motion of the clamping arms.

12. A flexible clamp according to claim 11 wherein the complementary interlocking structures comprise complementary projecting and recessed portions on each clamping arms such that the projecting and recessed portions of one clamping arm define an opposite or negative structure compared to the projecting and recessed portions of the other clamping arm.

13. A flexible clamp according to claim 11 wherein the complementary interlocking structures comprise complementary projecting and recessed portions on each clamping arm, the projecting portions of either clamping arm being closely received in the recessed portions of the other clamping arm when the clamping arms are in their closed position, thereby tending to prevent skewing of the free ends of the clamping arms out of the plane of motion of the clamping arms.

14. A flexible clamp according to claim 13 wherein the interlocking structures of the clamping arms are brought into pressing interengagement with one another when the clamping arms are in their closed position.

15. In an IV tubing set adapted for use with an infusion pump, the infusion pump being of the type comprising a pumping assembly including pumping means for pumping fluid through IV tubing to regulate fluid flow through the IV tubing, and releasable holding means for holding IV tubing during operation of the pumping assembly, clamp-receiving means on the pumping assembly for releasably receiving a clamp associated with the IV tubing, and releasable clamp-opening means for moving a clamp to an open position permitting fluid flow through the IV tubing, the clamp-receiving means and clamp-opening means being mounted in the infusion pump for movement relative to one another between an unloading position, wherein the clamp-opening means does not hold the arms of a flexible clamp received in the clamp-receiving means in their open position, and an operating position, wherein the clamp-opening means moves the arms of a flexible clamp received in the clamp-receiving means to their open position and holds the arms in the open position; the IV tubing set comprising:

IV tubing having a lumen through which fluid may be pumped for administration to a patient; and a flexible clamp associated with the IV tubing and adapted to be inserted in the clamp-receiving means of the infusion pump before operation of the infusion pump, the flexible clamp having a pair of generally elongate clamping arms defining a slot for receiving the IV tubing, the flexible clamp having a resilient bias tending to bring the clamping arms to a closed position wherein the IV tubing is squeezed between the clamping arms to close the lumen of the IV tubing to prevent fluid flow, the clamping arms being movable against the resilient bias of the flexible clamp by the clamp-opening means of the infusion pump to an open position wherein the clamping arms are spread from one another relative to the closed position such that the lumen of the IV tubing is allowed to open so that flow through the lumen of the IV tubing is permitted, the clamping arms having free ends movable relative to one another as the clamping arms are moved between their closed and open positions, the improvement comprising cooperable alignment means, on each clamping arm generally adjacent the free end of the clamping arm and cooperable with the cooperable alignment means of the other clamping arm, for aligning the free ends of each clamping arm relative to one another when the clamping arms are in their closed position, thereby tending to prevent skewing of the clamping arms when the clamping arms are in their closed position.

16. A tubing set according to claim 15 wherein the clamping arms define a plane of motion along which the clamping arms move between their closed and open positions, the cooperable alignment means comprises complementary interlocking structures on the free ends of the clamping arms that are brought into interlocking relationship when the clamping arms are brought to their closed position, thereby tending to prevent skewing of the free ends of the clamping arms out of the plane of motion of the clamping arms.

17. A tubing set according to claim 16 wherein the complementary interlocking structures comprise complementary projecting and recessed portions on each clamping arms such that the projecting and recessed portions of one clamping arm define an opposite or negative structure compared to the projecting and recessed portions of the other clamping arm.

18. A tubing set according to claim 16 wherein the complementary interlocking structures comprise complementary projecting and recessed portions on each clamping arm, the projecting portions of either clamping arm being closely received in the recessed portions of the other clamping arm when the clamping arms are in their closed position, thereby tending to prevent skewing of the free ends of the clamping arms out of the plane of motion of the clamping arms.

19. A tubing set according to claim 18 wherein the interlocking structures of the clamping arms are brought into pressing interengagement with one another when the clamping arms are in their closed position.

20. A tubing set according to claim 15 wherein the IV tubing has an outside diameter, and the slot defined by the clamping arms is a variable width slot along which the IV tubing may be moved between:
- a first position, wherein the width of the slot is relatively wide to permit the clamp to be positioned longitudinally along the IV tubing but is no wider than the outside diameter of the IV tubing so that the flexible clamp tends to hold its longitudinal position along the IV tubing; and
- a second position, wherein the width of the slot is normally less than the width of the slot in the first position and the clamping arms when in their closed position close the lumen of the IV tubing to fluid flow.

21. In an IV tubing set comprising:
IV tubing having a lumen through which fluid may flow to a patient; and
a flexible clamp associated with the IV tubing, the flexible clamp having a pair of generally elongate clamping arms defining a slot for receiving the IV tubing, the flexible clamp having a resilient bias tending to bring the clamping arms to a closed position wherein the IV tubing is squeezed between the clamping arms to close the lumen of the IV tubing to prevent fluid flow, the clamping arms being movable against the resilient bias of the flexible clamp to an open position wherein the clamping arms are spread from one another relative to the closed position such that the lumen of the IV tubing is allowed to open so that flow through the lumen of the IV tubing is permitted, the clamping arms having free ends movable relative to one another as the clamping arms are moved between their closed and open positions, wherein the improvement comprising cooperable alignment means, on each clamping arm generally adjacent the free end of the clamping arm and cooperable with the cooperable alignment means of the other clamping arm, for aligning the free ends of each clamping arm relative to one another when the clamping arms are in their closed position, thereby tending to prevent skewing of the clamping arms when the clamping arms are in their closed position.

22. A tubing set according to claim 21 wherein the clamping arms define a plane of motion along which the clamping arms move between their closed and open positions, the cooperable alignment means comprises complementary interlocking structures on the free ends of the clamping arms that are brought into interlocking relationship when the clamping arms are brought to their closed position, thereby tending to prevent skewing of the free ends of the clamping arms out of the plane of motion of the clamping arms.

23. A tubing set according to claim 22 wherein the complementary interlocking structures comprise complementary projecting and recessed portions on each clamping arms such that the projecting and recessed portions of one clamping arm define an opposite or negative structure compared to the projecting and recessed portions of the other clamping arm.

24. A tubing set according to claim 22 wherein the complementary interlocking structures comprise complementary projecting and recessed portions on each clamping arm, the projecting portions of either clamping arm being closely received in the recessed portions of the other clamping arm when the clamping arms are in their closed position, thereby tending to prevent skewing of the free ends of the clamping arms out of the plane of motion of the clamping arms.

25. A tubing set according to claim 24 wherein the interlocking structures of the clamping arms are brought into pressing interengagement with one another when the clamping arms are in their closed position.

26. A tubing set according to claim 25 wherein the IV tubing has an outside diameter, and the slot defined by the clamping arms is a variable width slot along which the IV tubing may be moved between:
- a first position, wherein the width of the slot is relatively wide to permit the clamp to be positioned longitudinally along the IV tubing but is no wider than the outside diameter of the IV tubing so that the flexible clamp tends to hold its longitudinal position along the IV tubing; and
- a second position, wherein the width of the slot is normally less than the width of the slot in the first position and the clamping arms when in their closed position close the lumen of the IV tubing to fluid flow.

27. In a free flow prevention system comprising:
IV tubing having an outside diameter and a lumen through which fluid may be pumped for administration to a patient;
a pumping assembly including pumping means for pumping fluid through the IV tubing, and releasable holding means for holding the IV tubing during operation of the pumping assembly;
a flexible clamp associated with the IV tubing and having a pair of clamping arms defining a variable width slot along which the IV tubing may be moved between a first position wherein the width of the slot is sufficient to permit the clamp to be positioned longitudinally along the IV tubing but is no wider than the outside diameter of the IV tubing so that the flexible clamp tends to hold its longitudinal position along the IV tubing, and a second position wherein the width of the slot is normally less than the width of the slot at the first position, the clamping arms being resiliently biased to a closed position wherein the IV tubing is squeezed when in its second position to close the lumen to prevent fluid flow, the clamping arms being movable against the bias to an open position wherein the lumen of the IV tubing is allowed to open so that flow through the lumen is permitted, the clamping arms having free ends movable relative to one another as the clamping arms are moved between their closed and open positions;

clamp-receiving means on the pumping assembly for releasably receiving the flexible clamp; and releasable clamp-opening means for separating the clamping arms of the flexible clamp and moving the arms from their closed position to the open position before operation of the pumping assembly;

the clamp-receiving means and clamp-opening means being mounted on the infusion pump for movement of the clamp-opening means relative to the flexible clamp received in the clamp-receiving means between an unloading position, wherein the clamp-opening means does not hold the arms of the flexible clamp in their open position, and an operating position, wherein the clamp-opening means moves the arms of the flexible clamp to their open position and holds the arms in the open position;

the improvement comprising the flexible clamp further comprising cooperable alignment means, on each clamping arm generally adjacent the free end of the clamping arm and cooperable with the cooperable alignment means of the other clamping arm, for aligning the free ends of each clamping arm relative to one another when the clamping arms are in their closed position, thereby tending to prevent skewing of the clamping arms when the clamping arms are in their closed position.

28. A free flow prevention system according to claim 27 wherein the clamping arms define a plane of motion along which the clamping arms move between their closed and open positions, the cooperable alignment means comprises complementary interlocking structures on the free ends of the clamping arms that are brought into interlocking relationship when the clamping arms are brought to their closed position, thereby tending to prevent skewing of the free ends of the clamping arms out of the plane of motion of the clamping arms.

29. A free flow prevention system according to claim 28 wherein the complementary interlocking structures comprise complementary projecting and recessed portions on each clamping arms such that the projecting and recessed portions of one clamping arm define an opposite or negative structure compared to the projecting and recessed portions of the other clamping arm.

30. A free flow prevention system according to claim 28 wherein the complementary interlocking structures comprise complementary projecting and recessed portions on each clamping arm, the projecting portions of either clamping arm being closely received in the recessed portions of the other clamping arm when the clamping arms are in their closed position, thereby tending to prevent skewing of the free ends of the clamping arms out of the plane of motion of the clamping arms.

31. A free flow prevention system according to claim 30 wherein the interlocking structures of the clamping arms are brought into pressing interengagement with one another when the clamping arms are in their closed position.

* * * * *